United States Patent [19]

Günther et al.

[11] Patent Number: 4,825,008

[45] Date of Patent: Apr. 25, 1989

[54] ACETYLKETENE DIALKYL ACETALS AND A PROCESS FOR THEIR PREPARATION

[75] Inventors: Klaus Günther, Eppstein; Günter Mau, Kelkheim, both of Fed. Rep. of Germany

[73] Assignee: Hoeschst Aktiengesellschaft, Frankfurt am Main, Fed. Rep. of Germany

[21] Appl. No.: 138,309

[22] Filed: Dec. 28, 1987

[30] Foreign Application Priority Data

Dec. 30, 1986 [DE] Fed. Rep. of Germany ....... 3644661

[51] Int. Cl.$^4$ ............................................. C07C 45/64
[52] U.S. Cl. ..................................... 568/391; 568/415
[58] Field of Search .............................. 568/391, 415

[56] References Cited

U.S. PATENT DOCUMENTS 2,570,713 10/1951 Richmond ............................ 568/391
3,932,520 1/1976 Hoffmann ............................ 568/415

FOREIGN PATENT DOCUMENTS 509390 8/1955 Canada ................................ 560/415
784610 5/1954 United Kingdom ................ 568/391

OTHER PUBLICATIONS

Hiroyama et al, Chem. Abst; vol. 86, #171491r (1977).
Chirila, Chem. Abst; vol. 88, #22780y (1978).
McElvain et al, "Mechanism of the Reaction of Ketene Acetal with Various Halides", J. Amer. Chem. Soc. 74, 2662–2667 (1952).

Primary Examiner—James H. Reamer

[57] ABSTRACT

The invention relates to a process for the preparation of acetylketene dialkyl acetals of the formula $CH_3CO-CH=C(OR^2)_2$ in which $R^2$ can be an alkyl radical with 1 to 12 carbon atoms, and also these compounds themselves, providing that $R^2$ is an alkyl radical with 3 to 12 carbon atoms. In the preparation process an alkyl acetoacetate of the formula $CH_3CO-CH_2COOR^1$ is reacted with a saturated primary or secondary alcohol $R^2OH$ in the presence of an acid catalyst, in which $R^2$ has the abovementioned meaning and in which $R^2OH$ or is higher boiling than $R^1OH$.

7 Claims, No Drawings

ACETYLKETENE DIALKYL ACETALS AND A PROCESS FOR THEIR PREPARATION

The invention relates to acetylketene dialkyl acetals and a process for their preparation. According to literature reports acetylketene diethyl acetal $CH_3-CO-CH=C(OC_2H_5)_2$ is prepared by reaction of ketene diethyl acetal with acetyl chloride, in which, however, considerable amounts of by-products result (McElvain, McShane, J. Am. Chem. Soc. 74, 1952, pages 2662, 2666). However, the starting substance ketene diethyl acetal is accessible with difficulty; its synthesis involves many reaction steps, which mostly proceed with unsatisfactory yields.

This process is therefore not very suitable for the preparation of acetylketene diethyl acetal on a larger scale. Furthermore, it is still only the existence of acetylketene dimethyl acetal that is mentioned in the literature. Acetylketene dialkyl acetals which contain higher alkyl groups than methyl and ethyl are not mentioned.

We have now found a simple process that enables acetylketene dialkyl acetals $CH_3-CO-CH=C(OR)_2$ having a wide range of alkyl groups to be obtained.

The invention relates to a process for the preparation of acetylketene dialkyl acetals of the formula $CH_3CO-CH=C(OR^2)_2$, in which $R^2$ can be an alkyl radical having 1 to 12 carbon atoms, which process comprises reacting an alkyl acetoacetate of the formula $CH_3CO-CH_2COOR^1$ in the presence of an acid catalyst with an alcohol of the formula $R^2OH$, in which $R^2$ has the abovementioned meaning and $R^2OH$ is either identical with $R^1OH$ or is higher boiling than $R^1OH$.

The invention furthermore relates to acetylketene dialkyl acetals of the formula $CH_3CO-CH=C(OR^2)_2$, in which $R^2$ is an alkyl radical with 3 to 12, preferably 3 to 8, carbon atoms.

Surprisingly, an acetylketene dialkyl acetal is formed in the process according to the invention without the formation of relatively large amounts of undesired, non-utilizable components.

In the reaction of an alkyl acetoacetate $CH_3COCH_2COOR^1$ with an alcohol $R^2OH$ which is higher boiling that the released alcohol $R^1OH$, transesterification occurs as a parallel reaction, i.e. in addition to the desired acetylketene dialkyl acetal $CH_3COCH=C(OR^2)_2$ an approximately equal amount of alkyl acetoacetate $CH_3COCH_2COOR^2$, which contains the alkyl group of the alcohol $R^2OH$ used as a co-reactant, is formed.

The lower boiling alcohol $R^1OH$ released in this reaction is completely removed by distillation so that finally the reaction mixture essentially only contains the acetylketene dialkyl acetal, $CH_3COCH=C(OR^2)_2$, the alkyl acetoacetate $CH_3COCH_2COOR^2$ formed by transesterification, and also the alcohol $R^2OH$, employed in excess. The reaction mixture obtained can be easily separated by fractional distillation, the acetylketene dialkyl acetal distilling over last as the highest boiling component.

Preferably, the reaction starts from the methyl or ethyl ester of acetoacetic acid; both compounds are readily available, especially the methyl ester. The alcohol $R^2OH$ necessary for the reaction is preferably employed in excess. In the case where $R^2OH$ is identical with $R^1OH$, 2.5 to 5 mol of alcohol are preferably employed per mol of acetoacetate; in the case where $R^2OH$ is higher boiling than $R^1OH$, 1.5 to 5 mol of the alcohol $R^2OH$ per mol of acetoacetate $CH_3COCH_2COOR^1$ are preferably employed.

Suitable alcohols $R^2OH$ are saturated primary and secondary, preferably primary, alcohols having 1 to 12 carbon atoms, preferably 3 to 6 carbon atoms, in which the carbon chain can be straight-chain or branched.

The reaction temperature should be about 110°–170° C., preferably 130°–160° C., in order to achieve a sufficiently high reaction rate. When the relatively low boiling alcohols $R^2OH$ having 1 to 3 carbon atoms are employed, it has proved expedient to carry out the reaction under a suitably elevated pressure, in order thereby to achieve the necessary reaction temperature of at least 110° C.

Acidic components are used as catalysts. Protonic acids, such as sulfuric acid, paratoluenesulfonic acid or phosphoric acid are preferably employed. Acidic ion exchangers and molecular sieves are also suitable. The concentration range for the catalyst employed is 0.005 to 5% by weight. A concentration of 0.05 to 0.2% by weight has proven very favorable when concentrated sulfuric acid is used.

On an industrial scale, the preparation of the acetylketene dialkyl acetals by the process according to the invention can be carried out discontinuously in a batch operation and also continuously in a suitably arranged apparatus.

In discontinuous production of the acetylketene dialkyl acetal from the methyl acetoacetate preferably employed, this ester is reacted in a first step with excess alcohol $R^2OH$ in which the highly volatile methanol liberated is recovered separately, and the excess alcohol $R^2OH$ together with the alkyl acetoacetate $CH_3COCH_2COOR^2$ obtained by transesterification are subsequently removed by distillation in vacuo, the acetylketene dialkyl acetal formed in this step remaining behind. In a second step the alkyl acetoacetate which is removed by distillation is allowed to react with excess alcohol $R^2OH$, again under the reaction conditions, to give acetylketene dialkyl acetal, and the excess alcohol $R^2OH$ together with the unreacted alkyl acetoacetate $CH_3COCH_2COOR^2$ is thereafter removed by distillation in vacuo, the acetylketene dialkyl acetal formed in the 2nd step remaining behind. To improve the yield, based on the methyl acetoacetate employed, the reaction can be repeated using the alkyl acetoacetate/excess alcohol mixture removed by distillation after the second step. The acetylketene dialkyl acetal formed in the individual steps is combined and jointly purified by vacuum distillation.

The continuous preparation of acetylketene dialkyl acetal can be carried out in a very elegant manner in an apparatus suitable for this purpose. Methyl acetoacetate together with excess alcohol $R^2OH$ catalyst are fed into a reactor. Methanol vapour, and the liquid reaction mixture, consisting of acetylketene dialkyl acetal $CH_3COCH=C(OR^2)_2$, alkyl acetoacetate $CH_3COCH_2COOR^2$ and alcohol $R^2OH$, are withdrawn from the reactor. The reaction mixture passes into a distillation column, in which the excess alcohol $R^2OH$ along with the unreacted alkyl acetoacetate distil off at the head. The head product is fed back into the reactor. The impure acetylketene dialkyl acetal is removed from the bottom of the column and is fed into a further column, in which it distils off at the head as a pure product. The catalyst and high-boiling residues are concentrated at the bottom of this column and are fed into a disposal plant.

The acetylketene dialkyl acetals are compounds which can be employed as starting materials for various syntheses. Due to their constitution they are particularly suitable for cyclization reactions. It is known that acetylketene dimethyl acetal and acetylketene diethyl acetal behave like 1-hydroxyvinylketene acetals at certain temperatures and, for example, give anthraquinones substituted in defined positions, which are of great importance as natural dyes (J. Chem. Soc. Perkin Trans. I, 1976, 17, 1872-56). This applies analogously to the homologs with longer alkyl radicals. The possibility of being able to prepare a wider range of acetylketene dialkyl acetals conveniently by the process according to the invention opens up a larger number of synthetic possibilities.

The following examples are intended to illustrate the invention.

EXAMPLE 1

174 g of methyl acetoacetate, 528 g of pentanol (mixture of about 85% by weight of pentan-1-ol and about 15% by weight of 1-methylbutan-1-ol) and 3.5 g of sulfuric acid were allowed to react for about 2.5 hours at 130°-140° C. in a 1 liter glass flask equipped with a condenser and stirrer. The condenser was thermostated at 90° C. so that low-boiling components could be removed by distillation. After completion of the reaction the reaction mixture contained 136 g of pentyl acetoacetate, 133 g of acetylketene dipentyl acetal, 344 g of pentanol, 5 g of methyl acetoacetate, 3.5 g of sulfuric acid and 26 g of unknown substances.

Acetylketene dipentyl acetal $CH_3COCH_2=C(OC_5H_{11})_2$ having a purity of greater than 99% by weight was obtained from the reaction mixture by fractional distillation (b.p. 120° C. at 3 mbar, $d_4^{20}=0.9200$, $n_D^{20}=1.4548$).

EXAMPLE 2

From a reaction mixture prepared as in Example 1, the excess pentanol and also the resulting pentyl acetoacetate were removed by distillation in vacuo from the acetylketene dipentyl acetal formed. The distillate contained 1210 g of pentanol, 671 g of pentyl acetoacetate and 24 g of other components. After addition of 2 g of sulfuric acid, the distillate was allowed to react for about 3 hours at 130° to 140° C. in the apparatus described in Example 1. After this, the reaction mixture comprised 1054 g of pentanol, 328 g of pentyl acetoacetate, 360 g of acetylketene dipentyl acetal and 38 g of other components. The reaction produced 127 g of distillate, of which 26% of weight was water.

EXAMPLE 3

1160 g of methyl acetoacetate, 2960 g of butan-1-ol and 4.4 g of sulfuric acid were allowed to react at about 120° C. in the apparatus described in Example 1. After 3.5 hours the reaction mixture contained 1388 g of butan-1-ol, 40 g of methyl acetoacetate, 1003 g of butyl acetoacetate, 588 g of acetylketene dibutyl acetal and 58 g of other components. The reaction produced 1048 g of distillate, which essentially comprised methanol, butanol and water. Acetylketene dibutyl acetal having a purity of above 99% could be recovered from the mixture by fractional distillation (b.p. 140°-142° C. at 20 mbar, $d_4^{20}=0.9390$; $n_D^{20}=1.4539$; elemental analysis (in % by weight) calculated 67.3% C; 10.3% H; 22.4% O; found: 67.2% C; 10.4% H; 22.2% O).

EXAMPLE 4

232 g of methyl acetoacetate, 714 g of pentan-1-ol and 1 g of sulfuric acid were allowed to react at 130° to 140° C. in the apparatus described in Example 1. After 2.5 hours the reaction mixture contained 487 g of pentan-1-ol, 188 g of pentyl acetoacetate, 173 g of acetylketene dipentyl acetal and 14 g of other components. The reaction produced 85 g of distillate, which essentially comprised methanol, acetone and water. Acetylketene dipentyl acetal with a purity of above 99% could be recovered from the mixture by fractional distillation (b.p. 145°-148° C. at 10 mbar; $d_4^{20}=0.9244$; $n_D^{20}=1.4564$; elemental analysis (in % by weight) calculated: 69.4% C; 10.7% H; 19.8% O; found: 69.4% C; 10.6% H; 19.8% O).

EXAMPLE 5

332 g of methyl acetoacetate, 816 g of hexan-1-ol and 1.3 g of sulfuric acid were allowed to react at 140° to 150° C. in the apparatus described in Example 1. After 3.5 hours the reaction mixture contained 520 g of hexan-1-ol, 260 g of hexyl acetoacetate, 177 g of acetylketene dihexyl acetal and 83 g of other components. The reaction produced 109 g of distillate, which essentially comprised methanol, acetone and water. Acetylketene dihexyl acetal having a purity of above 99% could be recovered from the mixture by fractional distillaton (b.p. 151°-153° C. at 3 mbar, $d_4^{20}=0.9177$; $n_D^{20}=1.4588$; elemental analysis (in % by weight) calculated: 71.1% C; 11.1% H; 17.8% O; found: 71.1% C; 11.0% H; 17.8% O).

EXAMPLE 6

332 g of methyl acetoacetate, 780 g of heptan-1-ol and 1 g of sulfuric acid were allowed to react at 150° C. in the apparatus described in Example 1. After 3.5 hours the reaction mixture contained 488 g of heptan-1-ol, 279 g of heptyl acetoacetate, 159 g of acetylketene diheptyl acetal and 70 g of other components. The reaction produced 117 g of distillate, which essentially comprised methanol, acetone and water.

EXAMPLE 7

116 g of methyl acetoacetate, 528 g of 2-ethyl-hexan-1-ol and 0.6 g of sulfuric acid were allowed to react at 150° C. in the apparatus described in Example 1. After 3.5 hours the reaction mixture contained 417 g of 2-ethyl-hexan-1-ol, 89 g of ethylhexyl acetoacetate, 65 g of acetylketene diethylhexyl acetal and 24 g of other components. The reaction produced 50 g of distillate, which essentially comprised methanol, acetone and water.

We claim:

1. A process for the preparation of acetylketene dialkyl acetals of the formula $CH_3CO-CH=C(OR^2)_2$, in which $R^2$ can be an alkyl radical with 1 to 12 carbon atoms, which process comprises reacting an alkyl acetoacetate of the formula $CH_3CO-CH_2COOR^1$ in the presence of an acid catalyst with a saturated primary or secondary alcohol of the formula $R^2OH$, in which $R^2$ has the above mentioned meaning and $R^2OH$ is either identical with $R^1OH$ or is higher boiling than $R^1OH$.

2. The process as claimed in claim 1, wherein the methyl or ethyl ester of acetoacetic acid is employed.

3. The process as claimed in claim 1, wherein, in the case where $R^2OH$ is identical with $R^1OH$, 2.5 to 5 mol of $R^2OH$ per mol of alkyl acetoacetate are employed.

4. The process as claimed in claim 1, wherein, in the case where $R^2OH$ is higher boiling than $R^1OH$, 1.5 to 5 mol of $R^2OH$ per mol of alkyl acetoacetate are employed.

5. The process as claimed in claim 1, wherein a primary alcohol $R^2OH$ is employed, in which $R^2$ is an alkyl radical with 3 to 6 carbon atoms.

6. The process as claimed in claim 1, wherein the reaction is carried out at a temperature of 130° to 160° C.

7. A process for the preparation of acetylketene dialkyl acetals of the formula $CH_3CO-CH=C(OR^2)_2$, in which $R^2$ can be an alkyl radical with 1 to 12 carbon atoms, which process comprises reacting an alkyl acetoacetate of the formula $CH_3CO-CH_2COOR^1$ at a temperature in the range of 110° to 170° C. in the presence of an acid catalyst with a saturated primary or secondary alcohol of the formula $R^2OH$, in which $R^2$ has the above mentioned meaning and $R^2OH$ is either identical with $R^1OH$ or is higher boiling than $R^1OH$.

* * * * *